United States Patent [19]
Chee et al.

[11] Patent Number: 5,304,194
[45] Date of Patent: * Apr. 19, 1994

[54] VASOOCCLUSION COIL WITH ATTACHED FIBROUS ELEMENT(S)

[75] Inventors: U. Hiram Chee, Palo Alto; Mike Mariant, Santa Clara, both of Calif.

[73] Assignee: Target Therapeutics, Fremont, Calif.

[*] Notice: The portion of the term of this patent subsequent to Jul. 13, 2010 has been disclaimed.

[21] Appl. No.: 956,724

[22] Filed: Oct. 2, 1992

Related U.S. Application Data

[63] Continuation-in-part of Ser. No. 771,013, Oct. 2, 1991, Pat. No. 5,226,911.

[51] Int. Cl.$^5$ .............................. A61B 17/00
[52] U.S. Cl. ................. 606/191; 606/198; 604/104; 604/52; 623/11
[58] Field of Search ............ 606/191, 198, 194, 200; 604/52, 53, 104, 105, 106; 623/1, 11, 12

[56] References Cited

U.S. PATENT DOCUMENTS

| | | | |
|---|---|---|---|
| 3,334,629 | 8/1967 | Cohn | 606/194 |
| 3,868,956 | 3/1975 | Alfidi et al. | 606/194 |
| 4,494,531 | 1/1985 | Gianturco | 606/200 |
| 4,655,771 | 4/1987 | Wallsten | 623/1 |
| 4,718,907 | 1/1988 | Karwoski et al. | 623/12 |
| 4,830,003 | 5/1989 | Wolff et al. | 606/191 |
| 4,856,516 | 8/1989 | Hillstead | 606/194 |
| 4,994,069 | 2/1991 | Ritchart et al. | 606/191 |
| 5,071,407 | 12/1991 | Termin et al. | 604/104 |

FOREIGN PATENT DOCUMENTS

| | | |
|---|---|---|
| 0183372 | 6/1986 | European Pat. Off. . |
| 0382014 | 8/1990 | European Pat. Off. . |
| 4102550 | 2/1990 | Fed. Rep. of Germany . |

OTHER PUBLICATIONS

Kumar et al., "Preoperative embolization of hypervascular head and neck neoplasms using microfibrillar collagen" *AJNR* (Mar./Apr. 1982) pp. 163-168.

*Primary Examiner*—Edgar S. Burr
*Assistant Examiner*—Christopher A. Bennett
*Attorney, Agent, or Firm*—Morrison & Foerster

[57] ABSTRACT

A device for occluding a blood vessel comprising a helical metal coil having at least one fibrous element attached to its proximal end wherein the fibrous element(s) extends in a sinusoidal wave configuration, the loops of which extend about individual windings at spaced intervals along the axis of the coil.

16 Claims, 3 Drawing Sheets

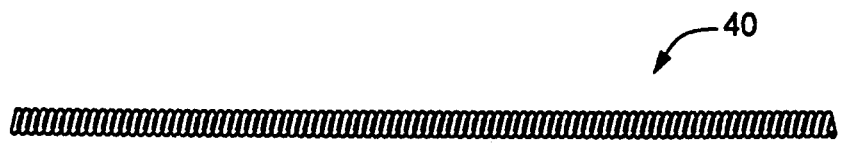
Fig. 3
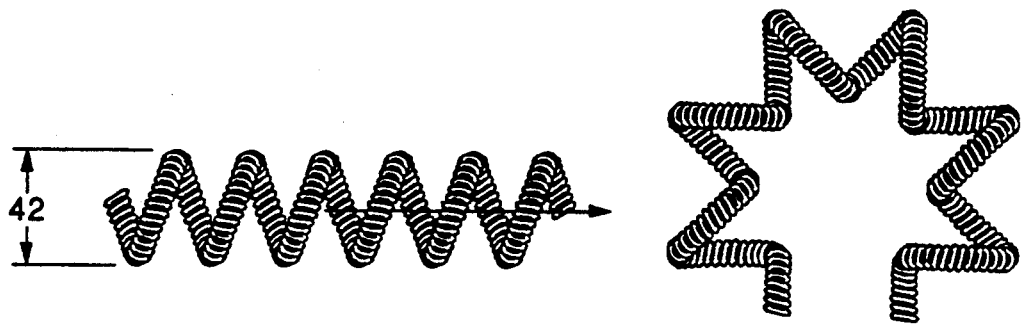
Fig. 4      Fig. 5
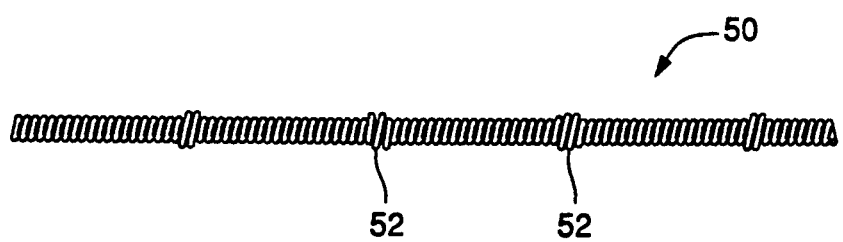
Fig. 9
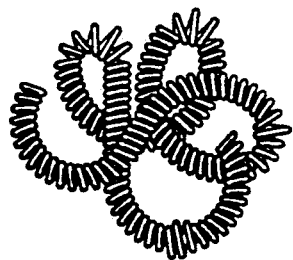 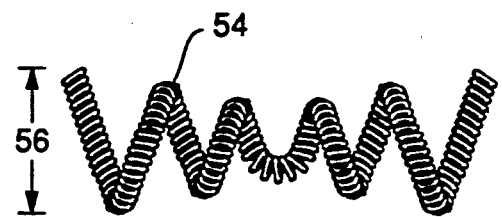
Fig. 10      Fig. 11

VASOOCCLUSION COIL WITH ATTACHED FIBROUS ELEMENT(S)

CROSS-REFERENCE TO A RELATED APPLICATION

This application is a continuation-in-part of U.S. Pat. application Ser. No. 07/771,013 filed Oct. 2, 1991, now U.S. Pat. No. 5,226,911, the disclosure of which is incorporated herein by reference.

TECHNICAL FIELD

This invention is in the field of vasoocclusion devices. More particularly it relates to a vasoocclusion coil to which fibrous elements are attached.

BACKGROUND

Vasoocclusion devices are surgical implements that are placed within vessels, typically via a catheter to block the flow of blood through the vessel. One type of vasoocclusive device is a helical wire coil that has windings that are dimensioned to engage the walls of the vessels. Fibers are laid crosswise through the windings to provide a substrate for embolization within the vessel. Coils of such structure are available commercially from Cook, Inc.

U.S. Pat. No. 4,994,069 describes a vasoocclusive coil that assumes a linear helical configuration when stretched and a folded convoluted configuration when relaxed. The stretched condition is used in placing the coil at the desired site and the coil assumes its relaxed configuration—which is better suited to occlude the vessel—once the device is so placed.

A principal object of the present invention is to provide a helical vasoocclusion coil to which fibrous elements are attached in a manner that ensures they will not be dislodged from the coil and enhances the ability of the coil to facilitate embolization.

DISCLOSURE OF THE INVENTION

The invention is a vasoocclusive device comprising:

(a) a helical coil having a multiplicity of windings extending between a first end and a second end;

(b) at least one fibrous element having a first end attached to one of said windings in the region of the first end of the coil, a second end attached to another of said windings in the region of the second end of the coil, with the portion of the element intermediate said ends extending axially along the coil in a generally serpentine configuration composed of a plurality of loops having maxima that extend radially outwardly and minima that extend radially inwardly and are threaded about individual windings at spaced intervals along the coil.

BRIEF DESCRIPTION OF THE DRAWINGS

FIGS. 1 to 11 are fragmentary elevational views (not to scale) of embodiments of the helical coil of the invention. FIGS. 1 and 2 show the specific manner of connecting the fibers to the coils.

In the drawings, like structures are referred to by the same reference numeral.

MODES FOR CARRYING OUT THE INVENTION

Figure 1:
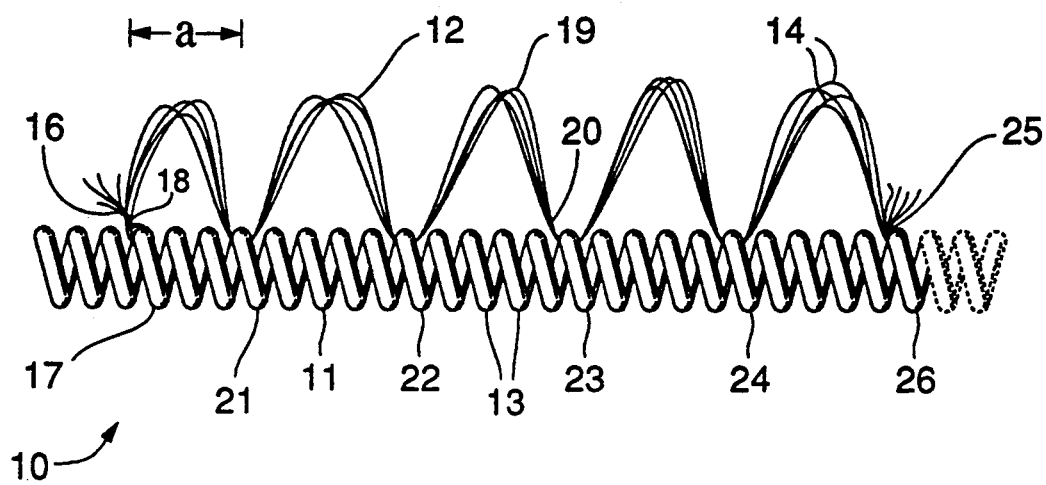

FIG. 1 depicts one embodiment, generally designated 10, of the vasoocclusive coil of the invention. The device 10 has two components: a helical coil 11; and a fibrous element 12.

Coil 11 will typically be made of a radiopaque material such as platinum, tungsten, gold, stainless steel, or of alloys such as tungsten and platinum. A tungsten-platinum alloy is preferred because of its strength and toughness. The material desirably is radiopaque and the diameter of the wire will usually be in the range of 0.05 to 0.25 mm. The coil has a multiplicity of individual windings 13. The axial length of the coil will usually be in the range of 0.2 to 100 cm, more usually 0.2 to 40 cm and the diameter of the coil will normally be 0.015 to 0.1 cm, more usually 0.025 to 0.1 cm. The coil will typically have about 10 to 70 windings per cm, more typically about 10 to 40 windings per cm.

In another aspect, the wire diameter of radiopaque coil 11 may be in the range of 0.05 to 0.25 mm. The coil has a multiplicity of individual windings 13. The axial length of the coil will usually be in the range of 0.2 to 100 cm, more usually 0.2 to 40 cm diameter of the coil will normally be 0.05 to 0.2 cm, more usually 0.05 to 0.15 cm. The coil will typically have about 5 to 70 windings per cm, more typically about 5 to 40 windings per cm. Such coils are especially suitable where large diameter coils or high strength coils are desirable, e.g., in large vessel occlusion.

Figure 2:
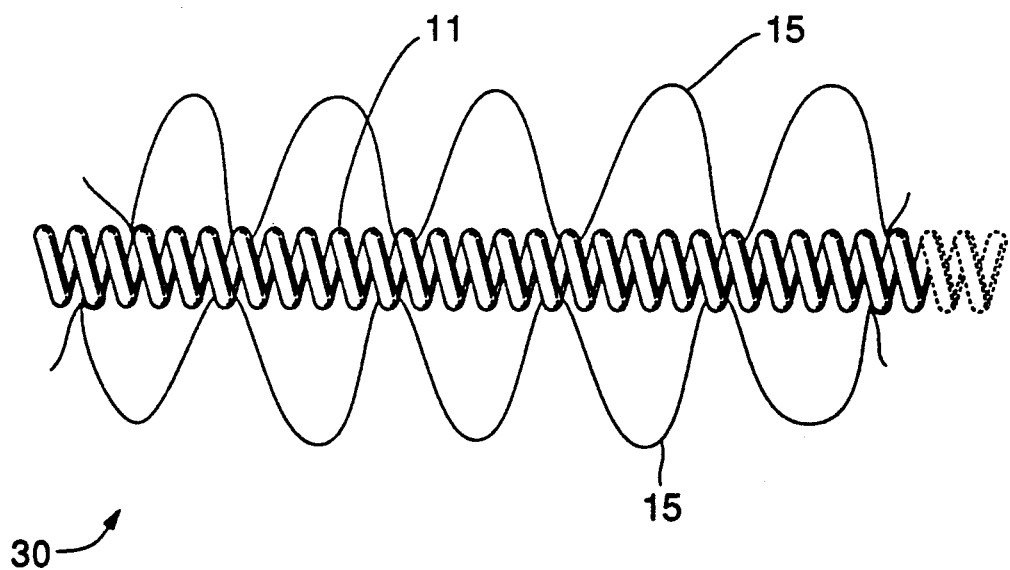

The fibrous element 12 may be a bundle of individual fibers 14 (typically 5 to 100 fibers per bundle, preferably 20 to 30 fibers per bundle) as shown in FIG. 1 or a monofilament 15 as shown in FIG. 2. The fibers may be made from biocompatible materials such as Dacron (polyester), polyglycolic acid, polyactic acid, fluoropolymer (polytetrafluoroethylene), nylon (polyamide), or silk.

In embodiment 10, end 16 of the bundle is tied to winding 17 of the coil by a knot 18. Knotting at the ends of the bundle is desirable, but not essential, as the threading of the loops about the windings (see below) is sufficient to anchor the bundle to the coil. The specific location of attachment of end 16 is not critical and it will typically be either at the proximal end 18 of the coil or at a site on the coil spaced from the proximal end a distance greater than the loop length (see below) when the loop is lying flat on the coil. The fiber bundle extends in a generally serpentine or sinusoidal wave configuration along the exterior of the coil in a series of outer-directed (relative to the coil axis) loops 19 and inner-directed loops 20. The inner directed loops are threaded about individual windings, designated 21, 22, 23 and 24 at spaced intervals (indicated as distance "a" between knot 18 and winding 21) along the coil. In FIG. 1, the individual windings are shown in a slightly expanded (spaced) condition for the purposes of illustration. More normally, however, the windings will be closer together so that the windings on either side of windings 21, 22, 23 and 24 pinch the fiber bundle against windings 21, 22, 23 and 24. The length of the intervals ("a") between the windings about which the fiber bundle passes may vary. It will typically be about 0.05 to 1 cm. The interval spacing may be the same or different along the length of the coil. Correspondingly, the loop length (e.g., the curvilinear length of the bundle from knot 18 to winding 21) may vary and may be the same or different from loop-to-loop. The loop length will normally be 0.1 to 2 cm, more usually 0.1 to 0.5 cm.

The fibrous element will usually extend between about 10% to 90% of the total axial length of coil. In other words, the axial distance over which the element extends will usually be 0.05 to 90 cm, more usually 0.05 to 15 cm. (The dashed lines in the drawings indicate that the coil extends distally.) The element will typically be located at the proximal end of the wire. In this regard, the term "proximal" is relative to orientation in which the coil is loaded within a catheter. The distal end of the element is affixed by knot 25 to winding 26.

While FIG. 1 depicts a coil with only a single affixed fiber bundle, it will be appreciated that a multiplicity (typically 2 to 4) of fiber bundles may be similarly attached at spaced intervals about the circumference of the coil.

FIG. 2 illustrates another embodiment, generally designated 30, of the vasoocclusive device of the invention. There are two differences between device 10 and device 30: (1) the fibrous element in FIG. 2 is a monofilament 15 and (2) there are two monofilaments 15 attached to the coil rather than a single fibrous element. As shown, the two monofilaments are spaced approximately 180° apart about the circumference of the coil. As in the case of device 10, additional monofilaments 15 may be affixed to the coil if desired.

FIGS. 3 to 11 show variants of the invention, but for simplicity of explanation, show the shape during introduction (FIGS. 3 and 9) or after introduction (FIGS. 4, 5, 6 to 8, 10 and 11) but without the invention fibers attached. The fibers are attached in the same way and in the same configuration as is shown in FIGS. 1 and 2.

FIG. 3 shows a partial side view of the helical coil 40 in the configuration found during installation. Typically the coil 40 will be placed on a wire core, which is interior to a catheter, which wire will hold the coil 40 in a linear form until discharged from the end of the wire.

FIG. 4 shows the coil of FIG. 3 after it has been released from the end of the guide or core wire. The coil loops back upon itself to form a secondary coil having a diameter 42. The secondary coil diameter 42 may be up to the size of the vessel to be occluded.

FIG. 5 shows the coil of FIG. 3 in which the coil has irregularities in the coil windings allowing formation of the folded convoluted conformation in the coil's relaxed condition. As seen, the multiple convolutions or irregularities in the embodiment are such as to offset the helical axis (the arrows in the FIG. 4) of each winding by 20–40 degrees.

Figure 6:
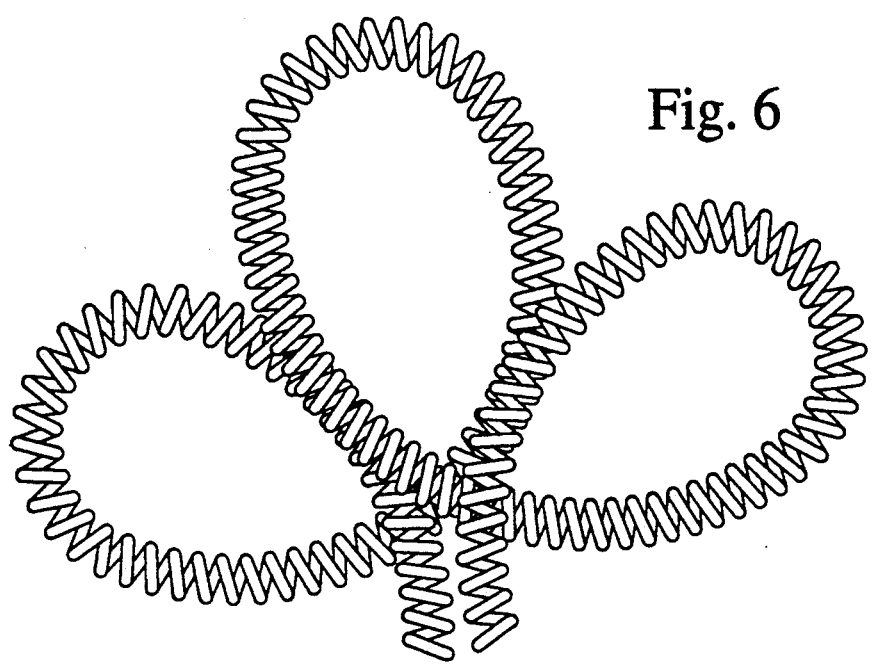
Figure 7:
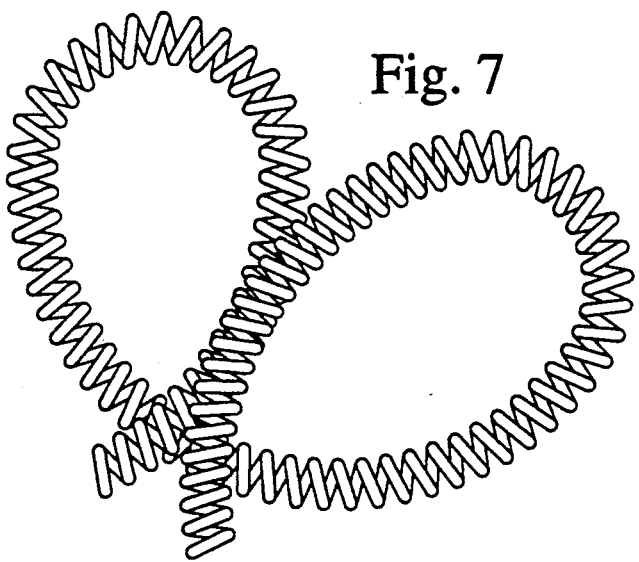
Figure 8:
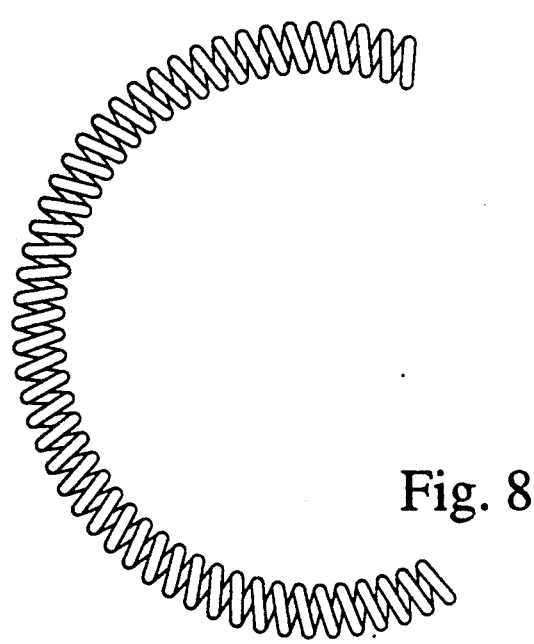

FIGS. 6, 7, and 8 each illustrate a different aspect of the invention. Whereas FIG. 1 and FIG. 2 show helical coils that are linear in shape, FIGS. 6–8 show differently shaped coils that are useful in the invention. FIG. 6 shows a cloverleaf-shaped vasoocclusive coil, FIG. 7 shows a twisted figure-8-shaped and FIG. 8 shows a C-shaped vasoocclusive coil. The fibers attached to these coils are analogous to the fibers attached to the coils in FIG. 1 and FIG. 2.

FIGS. 9 and 10 show a vasoocclusive coil such as is found above, but in which irregularities in the helical winding are produced by flattening the wire coil in different directions. This may be accomplished by flattening or squeezing the linear coil 50 in a number of places 52 along the winding at various angles (if so desired) such as shown in FIG. 9. The coil so formed will have the general appearance shown in FIG. 9 when in its linear configuration and those shown in FIG. 10 in its relaxed configuration. The flattened portions of the coil 52 must be smaller in diameter than the inner diameter of the catheter through which it must pass.

FIG. 11 shows a coil having a primary coil structure as described above, with a helical winding 54 having at least one helical turn whose diameter 56 is the size of the vessel to be occluded. In this variation, the irregularities in the helical winding take the form of continually changing helical diameters forming spirals which are dimensioned to span the cross-sectional area of the vessel.

Again, each of the variations shown in FIGS. 3 to 11 include the fibers independently shown in FIGS. 1 or 2.

The vasoocclusion coils of this invention are used in a manner similar to the coil of U.S. Pat. No. 4,994,069. Briefly, the coil is preferably supplied in prepackaged form in a sterile cannula which is adapted to engage the proximal end of a catheter. The loops of the fibrous bundle will be pressed flat against the coil for placement in the cannula and catheter. Once the catheter is in place within a vessel, the coil-containing cannula is placed into engagement with the proximal end of the catheter and the coil is transferred from the cannula lumen into the catheter lumen by exerting force on the proximal end of the coil. A pusher rod is used to push the coil through the catheter to the desired coil release site. The location of the coil may be visualized due to the radiopacity of the helical coil. Once at the site, the coil is plunged from the catheter lumen into the vessel. This allows the flexible fiber loops to extend outwardly from the coil surface to fill the vessel.

Modifications of the above-described modes for carrying out the invention that are obvious to those of skill in the fields of medical device design generally, and vasoocclusion specifically are intended to be within the scope of the following claims.

We claim:
1. A vasoocclusive device comprising:
   (a) a helical coil for occluding blood flow having a multiplicity of windings extending between a first end and a second end, said helical coil being from 2 to 100 cm in length and from 0.05 to 0.2 cm in diameter; and
   (b) at least one fibrous element having a first end and a second end, with the portion of the element intermediate said ends extending axially along the coil in a generally serpentine configuration composed of a plurality of loops having maxima that extend radially outwardly and minima that extend radially inwardly and are threaded about individual windings at spaced intervals along the coil.

2. The device of claim 1 wherein the fibrous element is attached to the proximal end of the helical coil and extends over about 10% to 90% of the length of the coil.

3. The device of claim 1 wherein there are a multiplicity of fibrous elements.

4. The device of claim 1 wherein there are 1 to 4 fibrous elements.

5. The device of claim 1 wherein the fibrous element is a bundle of individual fibers.

6. The device of claim 1 wherein the fibrous element is a monofilament.

7. The device of claim 1 wherein the length of an individual loop is 0.1 to 2 cm.

8. The device of claim 1 wherein said spaced interval is about 0.05 to 1 cm in length.

9. The device of claim 7 wherein said spaced interval is about 0.05 to 1 cm in length.

10. The device of claim 9 wherein the fibrous element is a bundle of about 5 to 100 individual fibers, there are 1 to 4 fibrous elements, the length of the helical coil is 2 to 100 cm, the fibrous elements are affixed to the proximal end of the helical coil, and the fibrous elements extend over about 25% to 50% of the length of the coil.

11. The device of claim 1 wherein the first end of the fibrous element is attached to one of said windings in the region of the first end of the coil and the second end is attached to another of said windings.

12. The device of claim 10 wherein the first end of the fibrous element is attached to one of said windings in the region of the first end of the coil and the second end is attached to another of said windings.

13. A vasoocclusive device comprising:
(a) a helical coil for occluding blood flow having a multiplicity of windings extending between a first end and a second end; and
(b) at least one fibrous element having a first end and a second end, with the portion of the element intermediate said ends extending axially along the coil in a generally serpentine configuration composed of a plurality of loops having maxima that extend radially outwardly and minima that extend radially inwardly and are threaded about individual windings at spaced intervals along the coil;
wherein said helical coil is in a conformation selected from the group consisting of a cloverleaf-shaped conformation, a twisted figure 8-shaped conformation and a C-shaped conformation.

14. The device of claim 13 wherein the helical coil is in a cloverleaf-shaped conformation.

15. The device of claim 13 wherein the helical coil is in a twisted figure 8-shaped conformation.

16. The device of claim 13 wherein the helical coil is in a C-shaped conformation.

* * * * *